United States Patent
Armstrong et al.

(10) Patent No.: US 6,228,150 B1
(45) Date of Patent: May 8, 2001

(54) CARBON DIOXIDE ABSORBENT IN ANAESTHESIOLOGY

(75) Inventors: John Raymond Armstrong, Balllymoney; James Murray, Belfast, both of (GB)

(73) Assignee: Armstrong Medical Limited, Londonderry (GB)

( * ) Notice: Subject to any disclaimer, the term of this patent is extended or adjusted under 35 U.S.C. 154(b) by 0 days.

(21) Appl. No.: 09/308,774
(22) PCT Filed: Nov. 25, 1997
(86) PCT No.: PCT/EP97/06698
§ 371 Date: Sep. 3, 1999
§ 102(e) Date: Sep. 3, 1999
(87) PCT Pub. No.: WO98/23370
PCT Pub. Date: Jun. 4, 1998

(30) Foreign Application Priority Data

Nov. 25, 1996 (GB) .................................................. 9624549
Nov. 14, 1997 (GB) .................................................. 9723990

(51) Int. Cl.[7] .................................................. B01D 53/04
(52) U.S. Cl. .............................. 95/139; 95/900; 96/108; 55/516
(58) Field of Search ...................... 95/139, 900; 423/230, 423/234; 96/108, 147; 55/512, 516, DIG. 5

(56) References Cited

U.S. PATENT DOCUMENTS

| | | | |
|---|---|---|---|
| 2,322,206 | | 6/1943 | Gardenier . |
| 2,848,309 | * | 8/1958 | Hay .................................. 423/230 X |
| 3,847,837 | * | 11/1974 | Boryta .............................. 423/230 X |
| 4,029,483 | * | 6/1977 | Long ...................................... 95/139 |
| 4,433,981 | * | 2/1984 | Slaugh et al. .......................... 95/139 |
| 4,492,649 | * | 1/1985 | Cheh et al. ....................... 423/230 X |
| 4,552,767 | * | 11/1985 | Saleeb et al. .................... 423/230 X |
| 4,946,620 | * | 8/1990 | Kadono et al. ..................... 95/139 X |
| 5,214,019 | * | 5/1993 | Nalette et al. ................... 423/230 X |
| 5,376,614 | * | 12/1994 | Birbara et al. ................... 423/230 X |
| 5,480,625 | * | 1/1996 | Nalette et al. ..................... 95/139 X |
| 5,595,949 | * | 1/1997 | Goldstein et al. ............... 423/230 X |

FOREIGN PATENT DOCUMENTS

| | | | |
|---|---|---|---|
| 2316214 | | 12/1973 | (DE) . |
| 2705533 | * | 8/1978 | (DE) ....................................... 95/900 |
| 3123064 | * | 1/1983 | (DE) ....................................... 95/139 |
| 530731 | | 3/1993 | (EP) . |

* cited by examiner

*Primary Examiner*—Robert H. Spitzer
(74) *Attorney, Agent, or Firm*—Baker Botts L.L.P.

(57) ABSTRACT

The invention concerns a carbon dioxide absorbent for use in anaesthesiology, in which the absorbent comprises at least one pharmaceutically acceptable hydroxide essentially free of sodium and/or potassium hydroxide and a carbon dioxide absorbingly effective amount of a compatible humectant. Calcium hydroxide is the preferred hydroxide. The humectant may be of inorganic or organic origin. The carbon dioxide absorbent of the invention may, additionally, include an effective amount of a setting agent, preferably calcium sulphate hemihydrate and/or a compatible agent for internal generation of hydrogen, preferably aluminium metal powder. The carbon dioxide absorbent of the invention is chemically inert to sevoflurane, as well as to the anaesthetics enflurane, isoflurane and desflurane.

38 Claims, 7 Drawing Sheets

CARBON DIOXIDE ABSORBENT IN ANAESTHESIOLOGY

This invention relates to a carbon dioxide absorbent which is intended to be used during low flow or closed circuit anaesthesia.

It has been known since 1789 (A.Lavoisier) that animals confined within closed vessels would continue to respire for a prolonged period, provided the vessel contained a carbon dioxide gas absorber. In the early 1880's, Professor Bert of Paris conducted experiments with small animals in closed vessels using chloroform vapour as anaesthetic and potassium hydroxide as a carbon dioxide absorber and reported toxic effects in the animals which he subsequently showed to be due to the decomposition products of the reaction of the chloroform with potassium hydroxide.

In 1914, D. E. Jackson first applied the carbon dioxide absorption principle of rebreathing to inhalational anaesthesia and therein commenced a search for efficient carbon dioxide absorbents which ended, at that time, with soda lime granules as the material of choice. Soda lime has been used since 1914 in conjunction with rebreathing anaesthesia and during this time many variations on the sodium and/or potassium hydroxide contents of the chemical composition have been made in an attempt to prevent excessive heating of the granules and to minimise crumbling and dust formation when the exothermic gas absorption process takes place.

Soda lime still remains the carbon dioxide absorbent of choice but it is far from ideal. For example, circuits containing organo-halogen anaesthetic vapours tend to chemically react with the sodium and/or potassium hydroxides in the soda lime granules by alkaline hydrolysis, or dehydrohalogenation, with the production of by-products which are very much more toxic than the anaesthetic itself. Just such a situation was reported in 1966 after the introduction of trichloroethylene (Trilene™). When trichloroethylene was used in the presence of soda lime as the carbon dioxide absorber, the alkaline hydrolysis product was dichloroacetylene whose rebreathing resulted in cranial nerve palsies in some individuals.

As would be expected, soda lime also reacts with the vapours of the modern fluoro-chloro anaesthetics. In 1992 the anaesthetic Sevoflurane™ was shown to undergo degradation in the presence of soda lime to a toxic olefin denoted "Compound A" of structure $CF_2=C(CF_3)OCH_2F$, which olefin is nephrotoxic to rats at concentrations of 60–100 ppm and lethal at concentrations of 350–400 ppm.

On a broader front, the literature teaches that the anaesthetics Enflurane™, Isoflurane™ and. Desflurane™ all react with soda lime under certain conditions and this has resulted in carbon monoxide poisoning in some individuals. The experimental evidence suggests that carbon monoxide is formed when these inhaled anaesthetics are used with dry soda lime, thereby producing formates, the probable precursors of the carbon monoxide. -Whilst the exact reactions have not yet been identified, it is thought that traces of fluoroform (trifLuoromethane; $CHF_3$) are produced which produce carbon monoxide under alkaline conditions. It is, therefore, recommended to use fresh or wet soda lime, to avoid generation of carbon monoxide.

U.S. Pat. No. 2,322,206 (published on Jun. 23, 1943) concerns a carbon dioxide absorbent bonded mixture, containing lime and barium hydroxide. The stability of the bonded mixture is ascribed to its non-hygroscocicity. EP-A-0 530 731 (published on Mar. 10, 1993) concerns a carbon dioxide absorbent containing a magnesium compound. When the magnesium compound is magnesium hydroxide, water is present. EP-A-0 530 731 discloses that, in contrast to calcium hydroxide, magnesium compounds hardly decompose certain anaesthetic gases. DE-A-2316214 (published on Dec. 20, 1973) concerns granular carbon dioxide absorbents comprising a travertine porous support, calcium hydroxide, water and a glycol. JP-A-58177137 (published on Oct. 17, 1983) concerns a carbon dioxide absorbent powder mixture for absorbing carbon dioxide generated by foods. The powder mixture may include an alkaline metal or alkaline earth metal hydroxide with an inorganic deliquescent material. The example includes sodium hydroxide and the dehydrate or hexahydrate of calcium chloride.

It is apparent therefore that there is a need in clinical practice for an efficient carbon dioxide removing agent, which is chemically inert (benign) to the anaesthetic itself.

It is an object of the present invention to fulfil this need by providing a carbon dioxide absorbent for use in low flow or closed circuit anaesthesiology comprising calcium hydroxide, the calcium hydroxide being essentially free of sodium and potassium hydroxide; and a hygroscopic or deliquescent inorganic humectant or a mixture thereof.

In a second aspect, there is provided use of a carbon dioxide absorbent in low flow or closed circuit anaesthesiology, the absorbent comprising calcium hydroxide, the calcium hydroxide being essentially free of sodium and potassium hydroxide; and a hygroscopic or deliquescent inorganic humectant or a mixture thereof.

The described carbon dioxide absorbent can be physically improved in terms of granule strength by preferably incorporating in the mixture an effective amount of a compatible setting agent, preferably Plaster of Paris (calcium sulphate hemihydrate), to increase the granule crushing strength.

It will be appreciated that any suitable setting agent may be used in the absorbent of the invention. It will also be appreciated that, as the amount of setting agent is increased, the absorbent's crushing strength is increased but the absorbent's absorptive efficiency is reduced. The amount of setting agent should, therefore, be kept as low as possible, so as to improve the absorbent's crushing strength whilst not significantly reducing the absorbent's absorptive efficiency. Thus, for plaster of paris, it is preferred to incorporate 4–5.5% (w/w), 4.5–5% (w/w) being more preferred.

The carbon dioxide absorbent may additionally comprise a compatible agent for internal generation of hydrogen, for example, a suitable amount of aluminium metal powder, to swell or "aerate" the granules before hardening, thereby improving the reactive surface area of the granules or pellets. Aluminium metal powder is preferred at 0.5–1% (w/w).

The basic concept in the present invention is the use of a hydroxide, preferably a hydroxide of low solubility in water (for example, calcium hydroxide, which is only soluble in water to the extent of 1 part in 900 of water) which nevertheless has a high capacity (reserve of acid neutralising power) for carbon dioxide absorption provided it can remain damp at all times. If such a permanent intrinsic moisture content can be achieved within the matrix of the hydroxide (preferably calcium hydroxide)-containing absorbent, without resorting to the hygroscopic property of the sodium or potassium hydroxide of soda lime, then carbon dioxide absorption can take place in low flow or closed circuit anaesthesiology without the production of either "Compound A" or carbon monoxide. Such permanent intrinsic moisture contents of the described absorbents are achieved by the incorporation of hygroscopic or deliquescent substances in the mix as humectants—these can be either inorganic or organic in nature.

The inorganic humectants must be hygroscopic (absorb atmospheric water) or deliquescent (absorb atmospheric water and dissolve in the water thus absorbed). The preferred inorganic humectants are hydroscopic or deliquescent hydrates. Suitable hydrates can be readily obtained by evaporation of an aqueous solution of a hydrate-forming compound. A preferred inorganic humectant is calcium chloride hexahydrate but a hydrate of magnesium chloride is also suitable. Although magnesium chloride hexahydrate reacts with calcium hydroxide to give magnesium hydroxide, the by-product of the reaction is calcium chloride, so that the matrix of the absorbent becomes a mixture of calcium and magnesium hydroxides kept permanently moist by the calcium chloride of the reaction.

The preferred inorganic humectant is calcium chloride hexahydrate which should preferably be present in an amount to yield, based on molecular weight, 7.5–20% (w/w), preferably about 10% (w/w) water.

Many suitable organic hygroscopic or deliquescent humectants may be incorporated in the carbon dioxide absorbents of this invention. Preferably, the organic humectant is a dihydric or polyhydric substance. Glycerol is preferred but other dihydric and polyhydric compounds can also be used with equal success including, but not limited to, propylene glycol, triethylene glycol, hexan-1,2,6-triol, polyethylene glycol 200 (PEG 200), PEG 300 and PEG 1540. In the case of the polyethylene glycols (PEG's), Martindale The Extra Pharmacopoeia (27th Edition) compares their hygroscopicity to that of glycerol (taken as 100) and, on this scale, PEG 200 is rated at 90 and PEG 1540 is rated at 30. Thus the lower molecular weight (liquid) PEG's are preferred to their solid class members. For glycerol, it is preferred to incorporate 2.5–25% (v/w), more preferably 2.5–10% (v/w), even more preferably about 5% (v/w).

The skilled person will realise that the absorbents of this invention need not be restricted to the individually cited inorganic and organic humectants and, in the case of the former, a deliquescent substance such as magnesium chloride can be employed to endow the mix with humectant properties even though its incorporation leads to a double decomposition reaction where the magnesium moiety becomes the hydroxide and the chloride moiety becomes calcium chloride, the eventual humectant The same is true for :he organic humectants where any alkali resistant non-reactive hygroscopic or deliquescent organic substance can be employed in aqueous solution as the powder's gauging medium.

Preferably, the carbon dioxide absorbent has a wager content of, for example, 17.5–30%, preferably 20–30% as measured by the Karl Fischer titration method described in Quantitative Chemical Analysis (pp485–6; Second Edition; Daniel C. Harris; W.H. Freeman and Company, New York).

It is preferred that the carbon dioxide absorbent of the invention should be in the form of granules or pellets of 1–8 mm diameter, more preferably 1–4 mm diameter.

Specific embodiments of the invention will now be described by way of the following formulation examples and with reference to the accompanying drawings in which.

EXAMPLE 1

| | |
|---|---|
| Calcium Hydroxide Powder | 750 g |
| Calcium Chloride Flakes | 200 g |
| Plaster of Paris | 45 g |
| Aluminium Metal Powder | 5 g |

To prepare the carbon dioxide absorbent in the form of granules, the above mixture of dry solids (1 kg) is gauged into a homogeneous paste with 11 water and, as soon as possible thereafter, extruded or shaped into granules and dried in an oven or hot air chamber at 70° C. for 1 hour, to a Karl Fischer moisture content of within She range 22–25%. Within 3–4 minutes of wetting, the alkalinity of the calcium hydroxide-containing paste reacts with the aluminium metal powder, to internally generate hydrogen gas but the alkalinity of the paste retards the setting of the Plaster of Paris thereby allowing sufficient time to extrude or shape the mix into granules (1–4 mm diameter) before hydration and setting of the Plaster of Paris takes place.

After the solids mixture of Example 1 is gauged with water, the calcium chloride flakes, which are classed commercially as anhydrous, dissolve in the water with evolution of heat and, on drying the granules, convert to calcium chloride hexahydrate. The hexahydrate is roughly 50% by weight $CaCl_2$ and 50% by weight water (molecular weight of $CaCl_2$ is 111 and molecular weight of the hexahydrate is 219.1). The hexahydrate has the convenient physical property of being efflorescent when the environment has a relative humidity (R.H.) below 20% and deliquescent when R.H. is above 30%.

Figure 1:
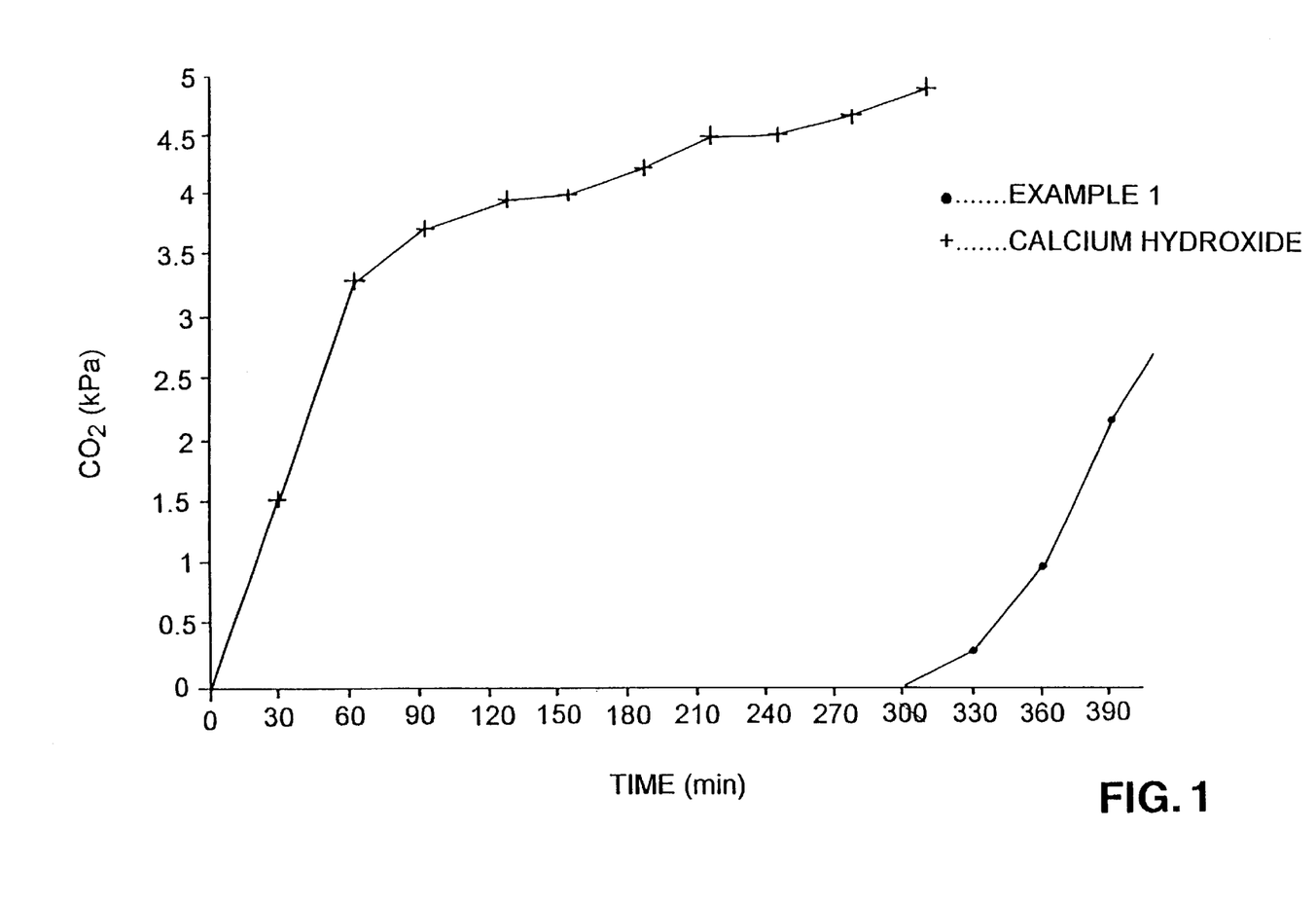
FIG. 1 shows the carbon dioxide absorptive capacity of calcium hydroxide and of the absorbent of Example 1.
Figure 2:
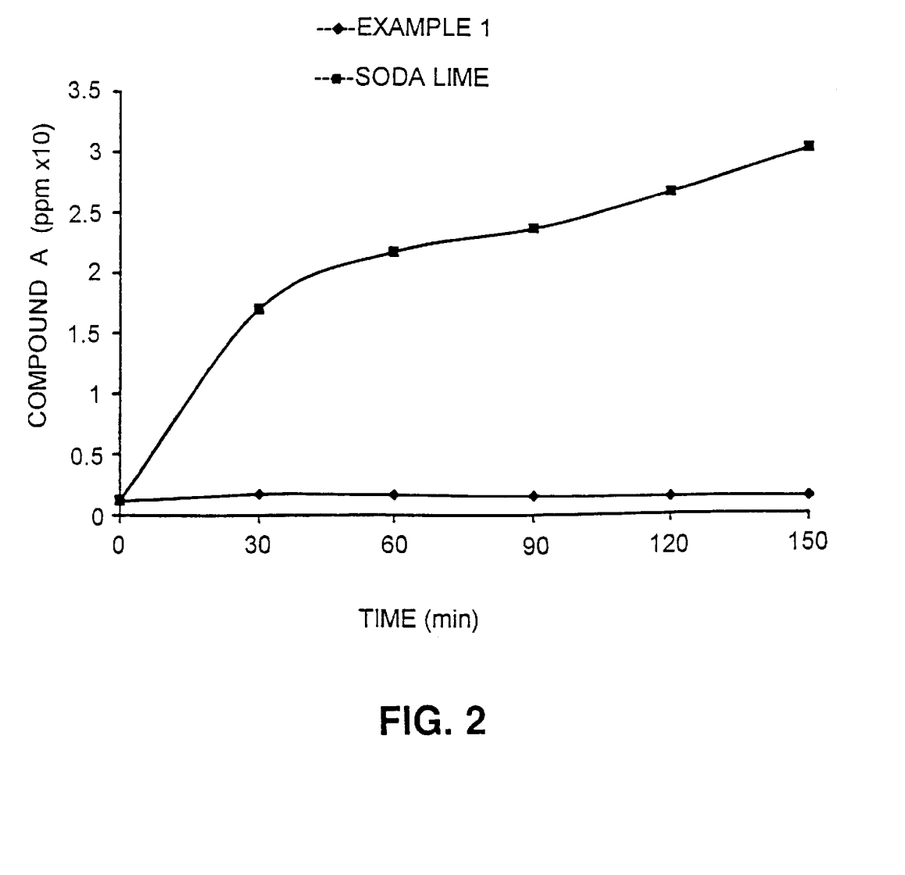
FIG. 2 shows "compound A" levels for soda lime and for the absorbent of Example 1 during low-flow anaesthesia.

Soda lime absorbs carbon dioxide because of its sodium and/or potassium hydroxide content. Dry calcium hydroxide alone is a poor absorber of carbon dioxide. The basic inventive step of creating the highly active carbon dioxide absorbent of the present invention, essentially free of sodium or/and potassium hydroxide, can be observed from the absorption curves of, for example, FIG. 1 where the carbon dioxide breakthrough times of similar granular amounts by weight of calcium hydroxide and those of Example 1 are about 300 minutes apart. In addition, the granules of Example 1 do not behave as hydrolytic agents—in closed circuit with the anaesthetic Sevoflurane™, negligible amounts of Compound A are observed when compared with soda lime granules under identical conditions (see FIG. 2). The traces of FIG. 2 have been computed from gas chromatograms of the gas stream circulating in the closed circuit of each experiment. The baseline Compound A levels observed with the absorbent of Example 1 are due to the small amounts of Compound A which are always present in the parent drug, Sevoflurane™.

Soda lime also suffers from the disadvantage that it progressively becomes coated with a layer of sodium carbonate, produced by interaction with the absorbed carbon dioxide, so that its activity falls off rapidly. In contrast, the compositions of the present Examples produce calcium carbonate as the end product of the carbon dioxide absorption process—calcium carbonate is insoluble in water and non-crystalline and, therefore, does not form surface blocking masses of interstitial crystals.

The humectant properties of calcium chloride hexahydrate mean that, when used in closed circuit anaesthesiology, the prepared granules of Example 1 are consistently damp and this is the state in which the calcium hydroxide content is most active as a carbon dioxide gas absorber. Experiments have indicated (see Example 3) that the optimum range of moisture content (as calculated from $CaCl_2.6H_2O$ content) in the absorbent granules is in the range 5 to 20% (w/w), preferably 7.5% to 17.5% (w/w), most preferably 10–15% (w/w).

This moisture retention can also be achieved by the substitution of polyhydric organic compounds for the calcium chloride hexahydrate of the granule mix. This effect is illustrated in the following example:

EXAMPLE 2

| Calcium Hydroxide Powder | 89.50 g |
| Plaster of Paris | 5.00 g |
| Glycerol | 5.00 ml |
| Aluminium Metal Powder | 0.50 g |

The glycerol (5 ml) is dissolved in 95 ml water and the solution (100 ml) is used to gauge the 95 g dry solids of the mix into a thick paste which can be extruded or shaped into granules (1–4 mm diameter). The granules are then dried at 70° C. for 1 hour, to a Karl Fischer moisture content of about 24–28%. Further water can be added, if desired, beyond the glycerol solution to gauge the 95 grams of powders. The carbon dioxide absorbent of Example 2 can be further modified to contain 10 ml, 15 ml and 20 ml glycerol, per 90, 85 and 80 g dry solids, by corresponding reductions in the respective calcium hydroxide contents—these absorbents are hereinafter denoted as containing 5%, (w/w), 10% (w/w), 15% (w/w) and 20% (w/w) glycerol based on original constituents (excluding water).

Figure 3:
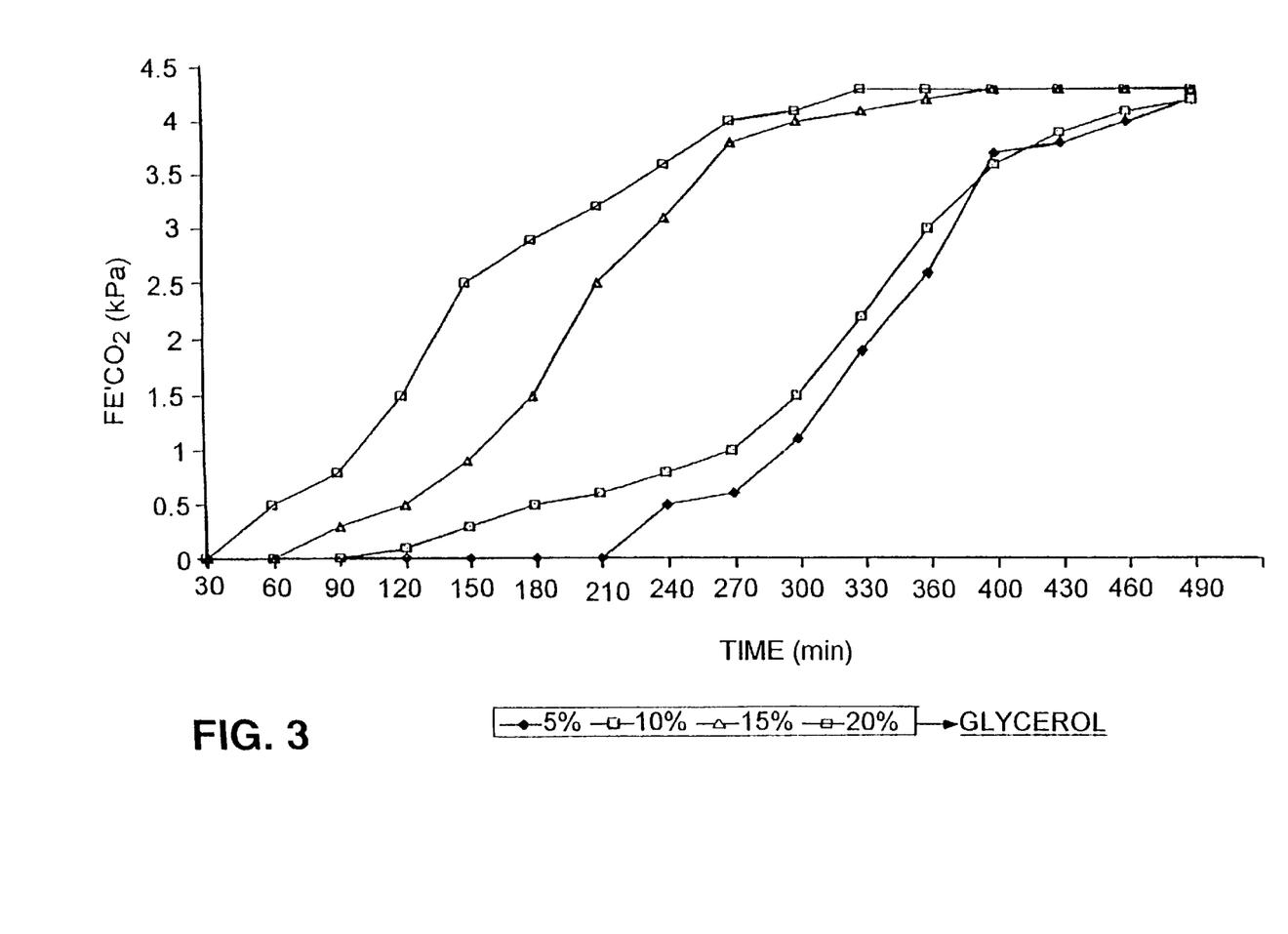
FIG. 3 shows the carbon dioxide absorption capacities for the absorbents of example 2.

The carbon dioxide absorption efficiencies of absorbents containing 5%, 10%, 15% and 20% glycerol are shown in FIG. 3. All of the absorbents tested show an improved absorptive capacity (area over curve) and a delayed breakthrough, i.e., when the $FE'CO_2$ level reaches 0.5 kPa, when compared with equivalent absorbents containing no humectant.

It will be appreciated from the data of FIG. 3 that glycerol is a preferred humectant. Glycerol is favoured for two reasons—firstly, the high absorption efficiency of the products (see FIG. 3) and, secondly, the fact that calcium hydroxide is more soluble in glycerol than in water, leading to higher absorbent absorption efficiencies because gas absorption can take place in both the solid and liquid phases of the granule's matrix.

EXAMPLE 3

| | Weight (g) | | | | |
|---|---|---|---|---|---|
| | A | B | C | D | E |
| Calcium Hydroxide Powder | 90 | 80 | 70 | 60 | 79 |
| Calcium Chloride Hexahydrate | 10 | 20 | 30 | 40 | 20 |
| Aluminium Metal Powder | — | — | — | — | 1 |

Carbon dioxide absorbents A–E were prepared by mixing 100 g of the dry solids. A control absorbent was prepared by using 100 g of the dry $Ca(OH)_2$ powder. Absorbents A–E contain, based on molecular weight, approximately 5, 10, 15, 20 and 10% (w/w) water, respectively.

The carbon dioxide absorption efficiencies of these carbon dioxide absorbents were immediately tested in the following manner.

A 50/50 mixture of oxygen and nitrous oxide was passed at a flow rate of 1 litre a minute through a canister containing 100 g of the absorbent to be tested. Carbon dioxide was added to the gas at between 55–60 ml/min, to maintain an end-tidal value of about 4.5 kPa. Samples were serially taken for carbon dioxide estimation, immediately downstream of the absorbent-containing canister.

The carbon dioxide absorbent is taken as being inefficient if a $FE'CO_2$ of 0.5 kPa is observed. This is defined as carbon dioxide breakthrough.

It will be appreciated that the capacity of the absorbent of the invention is dependent on its calcium hydroxide content. The carbon dioxide breakthrough figures quoted herein relate to 100 g absorbent under the above-mentioned experimental conditions.

Table 1 shows the carbon dioxide breakthrough values for a control absorbent (containing only dry calcium hydroxide) and for absorbents A–E of the invention.

TABLE 1

| | Carbon Dioxide breakthrough (minutes) |
|---|---|
| Control | 10 |
| A | 20 |
| B | 340 |
| C | 165 |
| D | 30 |
| E | 880 |

Figure 4:
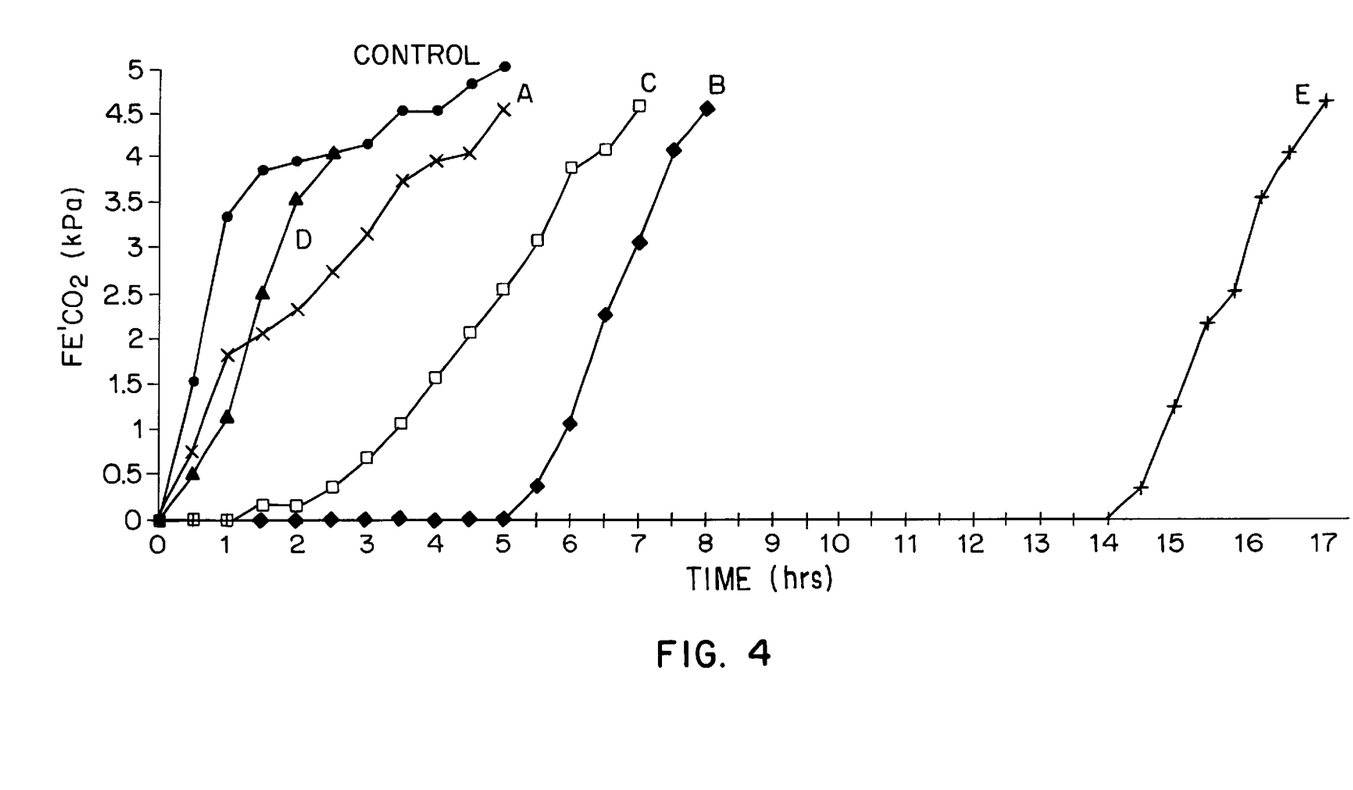
FIG. 4 shows the carbon dioxide absorption capacities for the absorbent of Example 3.

FIG. 4 shows the carbon dioxide absorption capacity over time in minutes, for the control absorbent and for absorbents A–E of the invention. The absorptive capacity of the respective materials is represented by the areas over the respective curves. Absorbent A shows a relatively early breakthrough whilst the area over the curve (absorptive capacity) was slightly improved, compared to the control absorbent. Absorbent B shows a remarkable improvement in absorptive capacity—the area over the curve is greatly increased; breakthrough does not occur for over 5 hours. Absorbent C shows, in comparison to control absorbent, an improved absorptive capacity, as well as, a delayed breakthrough at over 2½ hours. Absorbent D shows, in comparison to control absorbent, an improved absorptive capacity and a delayed breakthrough at about 30 minutes. Absorbent E, which contains, in addition, aluminium powder, shows a remarkable increase in absorptive capacity and remarkably prolonged breakthrough at well over 14 hours.

EXAMPLE 4

|  | Weight (g) |
| --- | --- |
| Calcium Hydroxide Powder | 845 |
| Calcium Chloride Flakes | 100 |
| Plaster of Paris | 45 |
| Aluminium Metal Powder | 10 |

The carbon dioxide absorbent was prepared by gauging the dry solids (1 kg) into a homogeneous paste with 11 water and immediately extruding or shaping the paste into pellets or granules (1–4 mm diameter), which are dried in an oven or hot air chamber at 70° C. for 1 hour to a moisture content (Karl Fischer titration method) of 20–25%.

It will be appreciated that a carbon dioxide absorbent in the form of granules prevents, or at least substantially reduces, release of dust into the test rig and, also, minimises resistance to flow.

Figure 5:
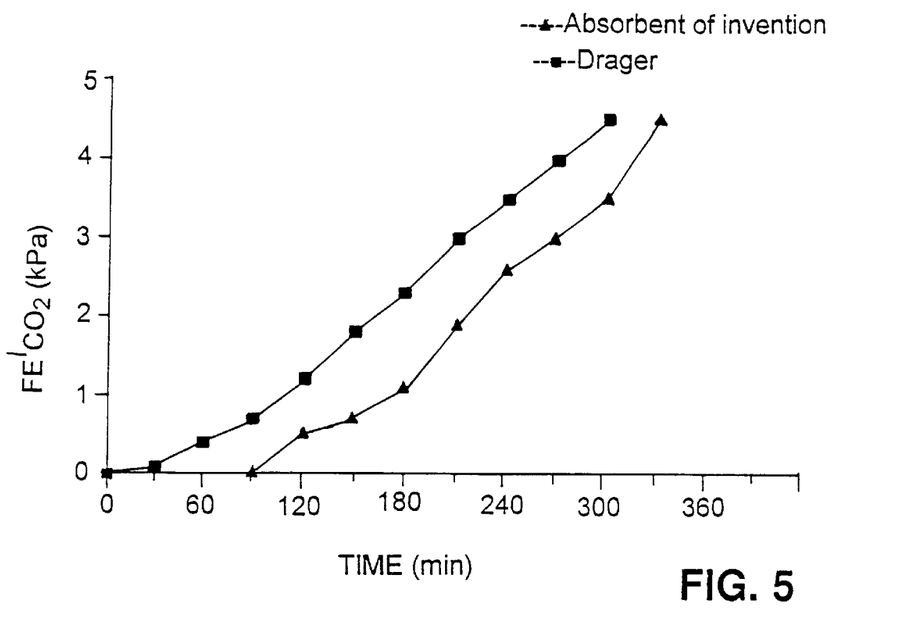
FIG. 5 shows the absorptive capacity of the absorbent of Example 4 when compared with a commercially available absorbent (Dragersorb (Trade Mark): 100 g)

FIG. 5 shows the absorptive capacity over time for the absorbent of Example 4. Breakthrough occurs after about 100 minutes and the area over the curve shows good absorptive capacity. Assuming a $CO_2$ flow rate of 55 ml/min, the absorptive capacity may be estimated as flow rate multiplied by time before breakthrough or 5.5 1 $CO_2$.

FIG. 5 also shows the absorptive capacity of 100 g of a commercially available absorbent, namely, supplied by Drager under the Trade Mark Dragersorb. The absorbent of the invention shows a better absorptive capacity and delayed breakthrough, when compared under identical conditions.

EXAMPLE 5

The ability of the absorbent of Example 2 (containing 5% (v/w) glycerol) to react with the anaesthetics Enflurane™, Isoflurane™ and Desflurane™, forming carbon monoxide, is assessed in the following manner.

Figure 6:
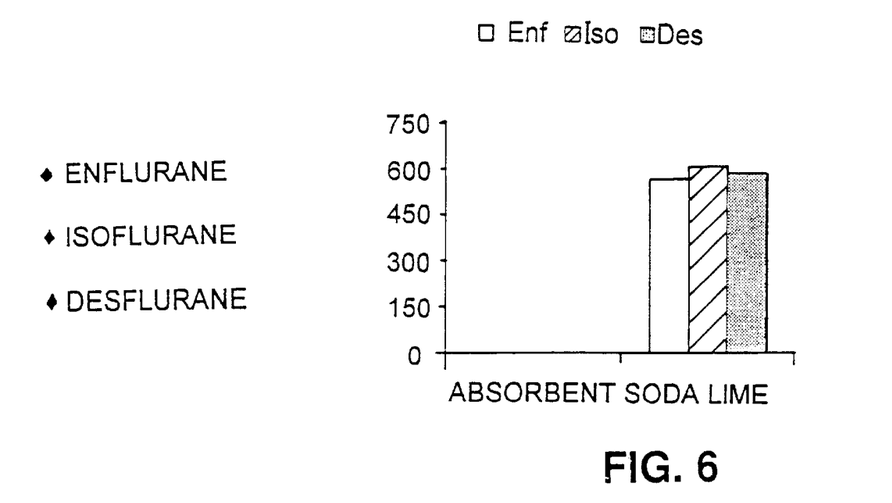
FIG. 6 shows the carbon monoxide levels (ppm) for the absorbent of Example 2 and for "dried out" soda lime.

Using the test rig described in Example 3, 100 g "dried our" soda lime was exposed to a 50/50 (v/v) nitrous oxide/oxygen mixture in the presence of 1 MAC of each anaesthetic agent. Carbon monoxide levels were measured with a CO meter immediately downstream of the canister outlet. Under these conditions, carbon monoxide was formed by enflurane, isoflurane and desflurane with "dried out" soda lime, as shown in FIG. 6. In contrast, when the absorbent of Example 2 is substituted for the "dried out" soda lime, there is no detectable formation of carbon monoxide, as shown in FIG. 6. Similar results (not shown) were observed when the absorbent of Example 1 is substituted for the absorbent of Example 2. Specifically, there was, also, no detectable formation of carbon monoxide in the presence of enflurane, isoflurane or desflurane.

EXAMPLE 6

|  | Weight (g) |
| --- | --- |
| Calcium Hydroxide Powder | 81.2 |
| Magnesium Chloride Hexahydrate | 18.8 |

The carbon dioxide absorbent is prepared by mixing the dry solids, to a water content (based on molecular weights) of 10% (w/w) water.

Figure 7:
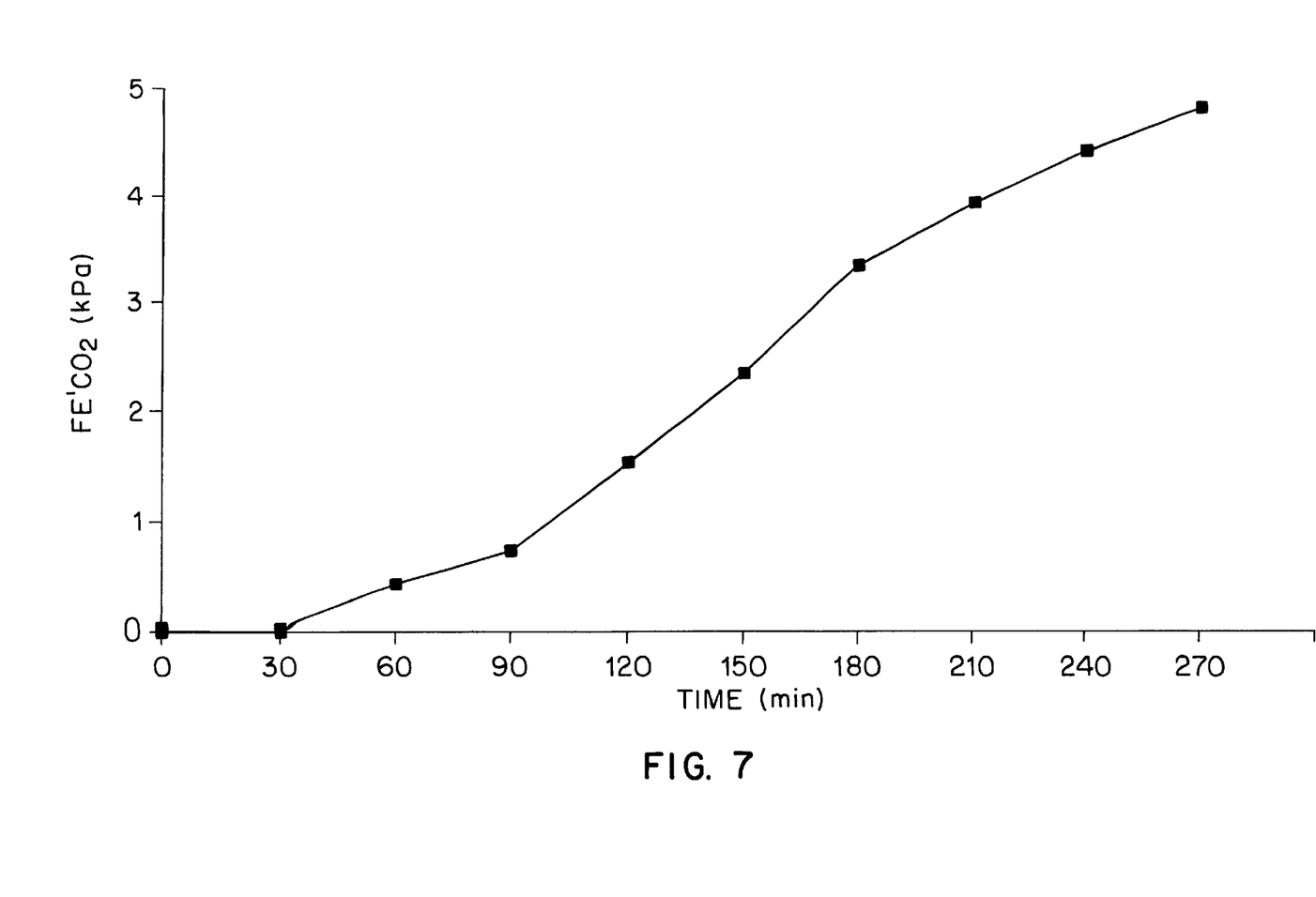
FIG. 7 shows the absorptive capacity for the absorbent of Example 6.

FIG. 7 shows the absorptive capacity over time for the absorbent of Example 6 when assessed under the experimental conditions of Example 3. Breakthrough occurs after about 70 minutes and the area over the curve shows good absorptive capacity.

EXAMPLE 7

|  |  |
| --- | --- |
| Calcium Hydroxide Powder | 95 g |
| Glycerol | 5 ml |

Figure 8:
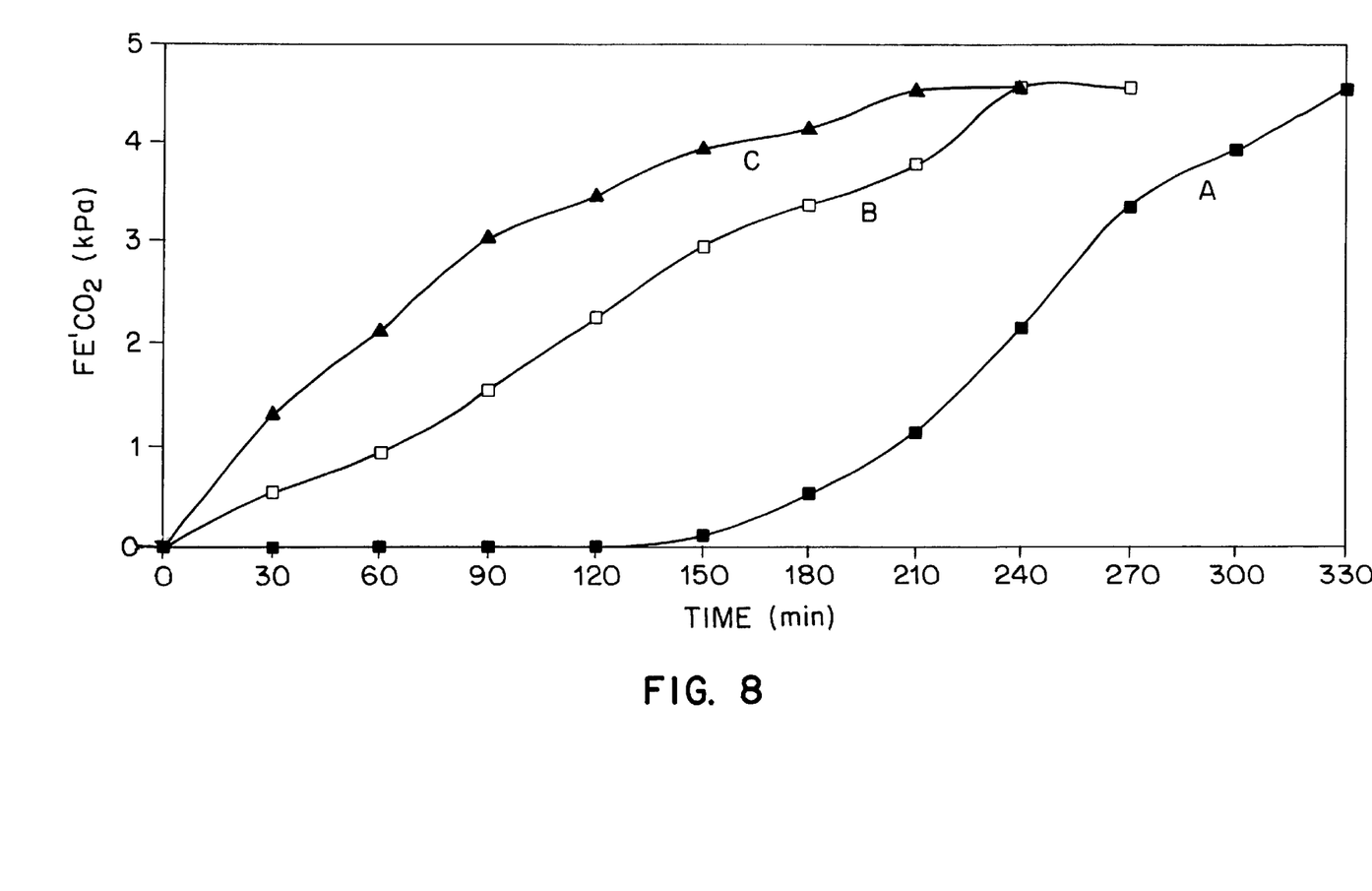
FIG. 8 shows the absorptive capacity for the absorbents of Example 7.

The glycerol (5 ml) is dissolved in 95 ml water and the glycerol solution is mixed with 95 g calcium hydroxide powder. When freshly made, the mixture has a water content of 35%, by the Karl Fischer titration method, which is a sensitive method which can be used for measuring residual water in purified solvents and water of hydration in crystals. Such a freshly made mixture does not exhibit any $CO_2$ absorption under the experimental conditions of Example 3. Following drying for one hour at 70° C., the water content of the mixture falls to 28% (Karl Fischer titration) and the period of time before $CO_2$ breakthrough is extended to 3 hours (identified as A on FIG. 8). Following drying for 2 hours at 70° C., the water content of the mixture falls to 19% (Karl Fischer titration) and the period of time before $CO_2$ breakthrough is 30 minutes (identified as B on FIG. 8). Following drying for 4 hours at 70° C., the mixture's water content has fallen to 15% (Karl Fischer titration) and the period of time before $CO_2$ breakthrough is just 7 mins (identified as C on FIG. 8). FIG. 8 shows the absorptive capacity over time for the absorbent of Example 7, when identical samples thereof were dried to a Karl Fischer water content of 28%, 19% or 15%, respectively. Assuming a $CO_2$ flow rate of 55 ml/min, the respective absorptive capacities of absorbents A, B and C are estimated as 9.9 l, 1.65 l and 0.385 l.

What is claimed is:

1. A method of absorbing carbon dioxide in low flow or closed circuit anaesthesiology, said method comprising the step of contacting a gas stream containing carbon dioxide with an absorbent, said absorbent comprising calcium hydroxide, and a hygroscopic or deliquescent inorganic humectant or a mixture thereof, wherein the calcium hydroxide is essentially free of sodium and potassium hydroxide.

2. The method according to claim 1, wherein said inorganic humectant is a hygroscopic or deliquescent hydrate.

3. The method according to claim 1, wherein said inorganic humectant is selected from the group consisting of calcium chloride hexahydrate, magnesium chloride hexahydrate, or a mixture thereof.

4. The method according to claim 3, wherein said inorganic humectant is calcium chloride hexahydrate, which is present in an amount sufficient to yield, based on molecular weight, from 7.5% to 20% (w/w) of water.

5. The method according to claim 1, wherein said absorbent further comprises an organic humectant.

6. The method according to claim 5, wherein said organic humectant is a dihydric or polyhydric substance.

7. The method according to claim 5, wherein said organic humectant is selected from the group consisting of glycerol, polyethylene glycol 200, polyethylene glycol 300, polyethylene glycol 1540, propylene glycol, hexan-1,2,6-triol, or a mixture thereof.

8. The method according to claim 5, wherein said organic humectant is glycerol, which is present at 2.5% to 25% (v/w).

9. The method according to claim 5, wherein the water content of the absorbent, as measured by Karl Fischer titration, is from 17.5% to 30%.

10. The method according to claim 5, wherein said absorbent further comprises an effective amount of a compatible setting agent.

11. The method according to claim 10, wherein the setting agent is calcium sulphate hemihydrate.

12. The method according to claim 10, wherein the setting agent is from 4% to 5.5% (w/w) calcium sulphate hemihydrate.

13. The method according to claim 10, wherein said absorbent further comprises a compatible agent for internal generation of hydrogen.

14. The method according to claim 13, wherein said compatible agent is aluminum metal powder.

15. The method according to claim 14, wherein the aluminum metal powder is present at 0.5 to 1% (w/w).

16. The method according to claim 5, wherein said absorbent further comprises a compatible agent for internal generation of hydrogen.

17. The method according to claim 1, wherein the water content of the absorbent, as measured by Karl Fischer titration, is from 17.5% to 30%.

18. The method according to claim 1, wherein said absorbent further comprises an effective amount of a compatible setting agent.

19. The method according to claim 1, wherein said absorbent further comprises a compatible agent for internal generation of hydrogen.

20. A carbon dioxide absorbent for use in low flow or closed circuit anaesthesiology, the absorbent comprising calcium hydroxide, and a hygroscopic or deliquescent inorganic humectant or a mixture thereof, wherein the calcium hydroxide is essentially free of sodium and potassium hydroxide.

21. The absorbent according to claim 20, wherein said inorganic humectant is a hygroscopic or deliquescent hydrate.

22. The absorbent according to claim 20, wherein said inorganic humectant is selected from the group consisting of calcium chloride hexahydrate, magnesium chloride hexahydrate, or a mixture thereof.

23. The absorbent according to claim 22, wherein said inorganic humectant is calcium chloride hexahydrate, which is present in an amount sufficient to yield, based on molecular weight, from 7.5% to 20% (w/w) of water.

24. The absorbent according to claim 20, further comprising an organic humectant.

25. The absorbent according to claim 24, wherein said organic humectant is a dihydric or polyhydric substance.

26. The absorbent according to claim 24, wherein said organic humectant is selected from the group consisting of glycerol, polyethylene glycol 200, polyethylene glycol 300, polyethylene glycol 1540, propylene glycol, hexan-1,2,6-triol, or a mixture thereof.

27. The absorbent according to claim 24, wherein said organic humectant is glycerol, which is present at 2.5% to 25% (v/w).

28. The absorbent according to claim 24, wherein the water content of the absorbent, as measured by Karl Fischer titration, is from 17.5 to 30%.

29. The absorbent according to claim 24, further comprising an effective amount of a compatible setting agent.

30. The absorbent according to claim 29, wherein the setting agent is calcium sulphate hemihydrate.

31. The absorbent according to claim 29, wherein the setting agent is from 4% to 5.5% (w/w) calcium sulphate hemihydrate.

32. The absorbent according to claim 29, further comprising a compatible agent for internal generation of hydrogen.

33. The absorbent according to claim 32, wherein said compatible agent is aluminum metal powder.

34. The absorbent according to claim 33, wherein the aluminum metal powder is present at 0.5% to 1% (w/w).

35. The absorbent according to claim 24, further comprising a compatible agent for internal generation of hydrogen.

36. The absorbent according to claim 20, wherein the water content of the absorbent, as measured by Karl Fischer titration, is from 17.5% to 30%.

37. The absorbent according to claim 20, further comprising an effective amount of a compatible setting agent.

38. The absorbent according to claim 20, further comprising a compatible agent for internal generation of hydrogen.

* * * * *